(12) United States Patent
Paradies et al.

(10) Patent No.: US 8,168,823 B2
(45) Date of Patent: May 1, 2012

(54) PROCESS FOR THE PREPARATION OF BETAINES

(75) Inventors: Gesa Paradies, Brig (CH); Markus Bicker, Visp (CH); Anton Zenklusen, Baltschieder (CH); Dario Veghini, Wohlen (CH)

(73) Assignee: Lonza Ltd, Basel (CH)

( * ) Notice: Subject to any disclaimer, the term of this patent is extended or adjusted under 35 U.S.C. 154(b) by 53 days.

(21) Appl. No.: 12/742,684

(22) PCT Filed: Nov. 14, 2008

(86) PCT No.: PCT/EP2008/009650
§ 371 (c)(1),
(2), (4) Date: May 13, 2010

(87) PCT Pub. No.: WO2009/062731
PCT Pub. Date: May 22, 2009

(65) Prior Publication Data
US 2010/0267986 A1    Oct. 21, 2010

(30) Foreign Application Priority Data

Nov. 16, 2007  (EP) ..................................... 07022273

(51) Int. Cl.
*C07C 229/00*  (2006.01)
(52) U.S. Cl. ..................................................... 562/567
(58) Field of Classification Search .......................... None
See application file for complete search history.

(56) References Cited

U.S. PATENT DOCUMENTS

| 4,708,936 A | * | 11/1987 | Kulla et al. | ................... 435/128 |
| 4,895,979 A |   | 1/1990  | Noyori et al. | |
| 5,545,667 A | * | 8/1996  | Wiersema et al. | ............ 514/556 |
| 5,696,287 A | * | 12/1997 | Bellis | ........................... 562/575 |

FOREIGN PATENT DOCUMENTS

| JP | 60161953 | | 8/1985 |
| JP | 60161953 A | * | 8/1985 |

OTHER PUBLICATIONS

XP002470890, Database WPI Week 198540, Thomson Scientific, London, GB; AN 1985-246175, 1985.
Zho B-N. et al., "Stereochemical Control of Yeast *Saccharomyces-cerevisiae* Reductions 1. Asymmetric Synthesis of L Carnitine", Journal of the American Chemical Society, vol. 105, No. 18, pp. 5925-5926; 1983.

* cited by examiner

*Primary Examiner* — Paul A Zucker
(74) *Attorney, Agent, or Firm* — Hoffmann & Baron, LLP

(57) ABSTRACT

Betaines of formula $R_3N^+$-Q-$COO^-$ (I), wherein R is $C_{1-4}$ alkyl and Q is $C_{1-4}$ alkanediyl, optionally substituted with hydroxy, are prepared in one step by adding an ω-halocarboxylate of formula X-Q-COOR' (II), wherein Q is as defined above, R' is $Cl_{1-4}$ alkyl and X is chlorine, bromine or iodine, to an aqueous solution containing a tertiary amine of formula $R_3N$ (III), Wherein R is as defined above and a base selected from alkali hydroxides and alkaline earth hydroxides. The process is particularly suited to the production of L-carnitine.

11 Claims, No Drawings

PROCESS FOR THE PREPARATION OF BETAINES

This application is the U.S. National Phase of, and Applicants claim priority from, International Application Number PCT/EP2008/009650 filed 14 Nov. 2008, and European Patent Application bearing Serial Number 07022273.2 filed 16 Nov. 2007, which are incorporated herein by reference in their entirety.

BACKGROUND OF THE INVENTION

The invention relates to a process for the production of betaines of formula $$R_3N^+\text{-Q-COO}^- \qquad (I),$$

wherein R is $C_{1-4}$ alkyl and Q is $C_{1-4}$ alkanediyl, optionally substituted with hydroxy. More specifically, the invention relates to a process for the production of carnitine. Carnitine (I, R=$CH_3$, Q=—$CH_2$—CHOH—$CH_2$—), and in particular the L-enantiomer of carnitine, is a vitamin-like substance that plays an important role in fatty acid metabolism.

L-Carnitine can be produced by biotechnological or chemical processes. U.S. Pat. No. 4,708,936 and U.S. Pat. No. 5,187,093 describe the production of L-carnitine by microbial biotransformation of butyro-betaine (I, R=$CH_3$, Q=—$(CH_2)_3$—). Several chemical processes involve the optical resolution of DL-carnitine. Other chemical processes are based on the asymmetric hydrogenation of γ-tri-methylammonioacetoacetates to L-carnitine esters (EP 0 375 417 A2), or the asymmetric hydrogenation of γ-chloroacetoacetates to L-γ-chloro-β-hydroxybutyrates which, in a subsequent step, are reacted with trimethylamine to the corresponding carnitine esters (U.S. Pat. No. 4,895,979). In both cases the L-carnitine esters are subjected to acid hydrolysis to yield a salt of L-carnitine (e.g. L-carnitine hydrochloride) which in turn has to be converted (e.g. by ion exchange) into the free betaine form of L-carnitine. These processes are relatively tedious and result in the formation of large amounts of salt byproducts which have to be disposed of.

JP-A-60-161952 discloses the production of carnitine from γ-chloro-β-hydroxybutyric acid or the methyl or propyl ester of γ-chloro-β-hydroxybutyric acid and trimethylamine in the presence of an alkali hydroxide. The reaction vessel is charged with the acid or ester and trimethylamine and alkali hydroxide are added either consecutively or as a mixture. The reported yields of carnitine are between 44% and 75%.

It is an object of the present invention to provide an improved chemical process for the production of L-carnitine and related betaines which gives the desired products in high yield and does not require a separate hydrolysis step.

According to the invention, this object has been achieved by the process of claim 1.

DESCRIPTION OF THE INVENTION

It has been found that the yield and purity of the desired product can be significantly improved if the ω-halocarboxylate is added to the solution of the amine and the base, instead of adding the amine and the base to the ω-halocarboxylate. This is somewhat surprising since one might expect that side reactions (e.g., elimination instead of substitution) could predominate if an excess of base is present during the reaction.

According to the invention, an ω-halocarboxylate of formula $$\text{X-Q-COOR'} \qquad (II),$$

wherein Q is $C_{1-4}$ alkanediyl, R' is $C_{1-4}$ alkyl and X is chlorine, bromine or iodine, is reacted with a tertiary amine of formula $$R_3N \qquad (III),$$

wherein R is $C_{1-4}$ alkyl,
by adding the ω-halocarboxylate (II) to an aqueous solution containing the tertiary amine (III) and a base selected from alkali hydroxides and alkaline earth hydroxides, to obtain a betaine of formula $$R_3N^+\text{-Q-COO}^- \qquad (I),$$

wherein Q and R are as defined above.

The reaction can be conducted at relatively low temperatures and without elevated pressure.

Advantageously, the ω-halocarboxylate is added slowly to an agitated aqueous solution containing the tertiary amine and the base. The time of addition is typically between 15 min and 6 h, preferably about 3 h. The reaction temperature is preferably between the freezing point of the aqueous reaction mixture and +25° C. More preferably, the reaction temperature is +10° C. or less, still more preferably +6° C. or less and most preferably +3° C. or less.

The tertiary amine and the base are preferably used in an amount of 1 to 3 equivalents each, based on the amount of ω-halocarboxylate. More preferably, the base is used in an amount of 1 to 2 equivalents and most preferably 1.5 equivalents or less.

In a preferred embodiment, the substituents R are methyl groups.

In another preferred embodiment, Q is 2-hydroxypropane-1,3-diyl (—$CH_2$—CHOH—$CH_2$—) and the betaine produced is carnitine. More preferably, the betaine is L-carnitine.

The halogen X in the ω-halocarboxylate (II) is preferably chlorine.

The substituent R' in the ω-halocarboxylate (II) is preferably methyl or ethyl.

The base is preferably sodium hydroxide or potassium hydroxide.

The betaine can be isolated and purified using methods known in the art. The alcohol R'OH formed in the reaction and excess tertiary amine $R_3N$ as well as part of the water used as solvent can be removed by distillation, preferably under reduced pressure. The excess amine may be recovered and recycled.

The salt byproduct is preferably removed by electrodialysis, advantageously after removing the volatile components as described above. Depending on the moiety Q in the ω-halocarboxylate starting material, some dehydrohalogenation (elimination of hydrogen halide), elimination of water, and/or hydrolysis instead of substitution may take place as a side reaction. In particular, when a γ-chloro-β-hydroxybutyrate is used as starting material, some γ-hydroxycrotonic acid will be formed by elimination of water and hydrolysis of the chloro function. This (non-betaine) byproduct is also removed by electrodialysis. The betaine (I) can be isolated by conventional methods, e.g. by distilling off the water from the diluate obtained after electrodialysis.

The process of the invention can be performed batchwise or continuously, e.g. in a continuous stirred-tank reactor or a cascade of continuous stirred-tank reactors.

The following non-limiting examples illustrate the process of the invention. With the exception of the yields, all percentages are given in weight percent, unless otherwise specified.

Example 1

L-Carnitine (I, R=CH$_3$, Q=—CH$_2$—CHOH—CH$_2$—)

Sodium hydroxide (17.6 g, 0.44 mol, ca. 2 eq.) was dissolved in water (240 g). Aqueous tri-methylamine (25%, 61.3 g, ca. 1.2 eq.) was added with cooling. The resulting mixture was cooled to 0° C. and ethyl (R)-4-chloro-3-hydroxybutyrate (content 100%, 36 g, 0.216 mol) was added dropwise within 3 h to the stirred reaction mixture. After one additional hour at 0° C. the reaction mixture was warmed to +20° C. and analyzed by HPLC
Yield: 80% L-carnitine

Example 2

L-Carnitine

The procedure of Example 1 was repeated using 1.2 equivalents of sodium hydroxide and 2.5 equivalents of trimethylamine. L-Carnitine was obtained in essentially the same yield (81%).

Example 3

L-Carnitine

Water (1777 g), aqueous sodium hydroxide (50%, 203.7 g, 1.5 eq.) and aqueous trimethylamine (25%, 807 g, 2.0 eq.) were mixed and stirred at 0° C. Ethyl (R)-4-chloro-3-hydroxybutyrate (content 91.7%, 307.9 g) was added dropwise during 3 h and the procedure was continued as described in Example 1.
Yield: 89% L-Carnitine

Example 4

L-Carnitine (Continuous Process)

An aqueous solution of sodium hydroxide (3.9%) and trimethylamine (5.7%) was fed into the first stirred tank of a cascade of five 250 mL continuous stirred-tank reactors while ethyl (R)-4-chloro-3-hydroxybutyrate was fed in equal amounts into the first four reactors. The mean residence time in each reactor was approx. 1 h and both trimethylamine and sodium hydroxide were used in an amount of 1.0 eq., based on the total amount of ethyl (R)-4-chloro-3-hydroxy-butyrate. The temperature of all reactors was maintained at 0° C. Once a steady state had been established, the yield of L-carnitine was 80-83%

COMPARATIVE EXAMPLE 1

L-Carnitine

Ethyl (R)-4-chloro-3-hydroxybutyrate (content: 95.5%, 30.0 g, 0.172 mol) was stirred at 0° C. while a mixture of trimethylamine (25% aqueous solution, 90.7 g, 0.383 mol), sodium hydroxide (content: 98.5%, 7.82 g, 0.193 mol) and deionized water (136 g) was added dropwise during 2 h. After an additional hour the L-carnitine content of the reaction mixture was determined by HPLC: 7.35%, corresponding to 70% yield. The reaction mixture was concentrated in vacuo and analyzed by $^1$H NMR. It was found to contain some γ-hydroxycrotonic acid and an unidentified olefinic byproduct.

Example 5

L-Carnitine

Sodium hydroxide (156.1 g, 3.9 mol, 1.4 eq) was dissolved in water (3700 g). Aqueous tri-methylamine (25%, 649.5 g, 1.0 eq) was added with cooling. The resulting mixture was cooled to 0° C. and ethyl (R)-4-chloro-3-hydroxybutyrate (content 91.5%, 500.0 g, 2.75 mol) was added dropwise within 3 h to the stirred reaction mixture. After one additional hour at 0° C. the reaction mixture was warmed to +20° C. and analyzed by HPLC.
Yield: 85% L-Carnitine

COMPARATIVE EXAMPLE 2

L-Carnitine

In a 250 mL reactor, ethyl (R)-4-chloro-3-hydroxybutyrate (content 94%, 12.00 g, 67.7 mmol) was stirred with water (75.04 g) and cooled to 0° C. Aqueous trimethylamine (25%, 17.71 g, 1.1 eq.) was added at once at 0° C., followed by dropwise addition of aqueous sodium hydroxide (25%, 15.30 g, 1.4 eq.) within 3 h. After another 1 h at 0° C. the reaction mixture was allowed to warm to 20° C. and analyzed by HPLC.
Yield: 76% L-Carnitine (HPLC/IC)

COMPARATIVE EXAMPLE 3

L-Carnitine

The procedure of Comparative Example 2 was repeated with the exception that the aqueous sodium hydroxide was added at once, followed by dropwise addition of the aqueous trimethyl-amine within 3 h.
Yield: 75% L-Carnitine (HPLC/IC)

COMPARATIVE EXAMPLE 4

L-Carnitine

The procedure of Comparative Example 2 was repeated with the exception that the aqueous trimethylamine and the aqueous sodium hydroxide were added separately but simultaneously within 3 h.
Yield: 77% L-Carnitine (HPLC/IC)

The invention claimed is:
1. A process for the production of a betaine of formula

$$R_3N^+\text{-Q-COO}^- \quad (I),$$

wherein R is C$_{1-4}$ alkyl and Q is C$_{1-4}$ alkanediyl, optionally substituted with hydroxy, by reacting, in aqueous solution, an ω-halocarboxylate of formula $$\text{X-Q-COOR}' \quad (II),$$

wherein Q is as defined above, R' is C$_{1-4}$ alkyl and X is chlorine, bromine or iodine, with a tertiary amine of formula $$R_3N \quad (III),$$

wherein R is as defined above and a base selected from alkali hydroxides and alkaline earth hydroxides, characterized in that the w-halocarboxylate (II) is added to an aqueous solution comprising the tertiary amine (III) and the base.

2. The process of claim 1, wherein the reaction is conducted at a temperature between the freezing point of the reaction mixture and +25° C.

3. The process of claim 2, wherein the reaction is conducted a temperature of no more than +10° C.

4. The process of claim 1, wherein the tertiary amine (III) and the base are used in an amount of 1.0 to 3 equivalents each, based on the amount of ω-halocarboxylate.

5. The process of claim 1, wherein R is methyl.

6. The process of claim 1, wherein Q is 2-hydroxypropane-1,3-diyl and the betaine (I) is carnitine.

7. The process of claim 6, wherein the betaine (I) is L-carnitine.

8. The process of claim 1, wherein X is chlorine.

9. The process of claim 1, wherein R' is methyl or ethyl.

10. The process of claim 1, wherein the base is sodium hydroxide or potassium hydroxide.

11. The process of claim 1, wherein the betaine (I) is purified by electrodialysis.

* * * * *